United States Patent [19]

Ikenoue et al.

[11] 3,960,908

[45] June 1, 1976

[54] PROCESS FOR PREPARING ORGANOSILVER CARBOXYLATES

[75] Inventors: Shinpei Ikenoue; Takao Masuda, both of Asaka, Japan

[73] Assignee: Fuji Photo Film Co., Ltd., Minami-ashigara, Japan

[22] Filed: Jan. 21, 1974

[21] Appl. No.: 435,127

[30] Foreign Application Priority Data

Jan. 22, 1973 Japan.................................. 48-9362

[52] U.S. Cl.............................. 260/414; 96/94 R; 96/114.1; 260/430
[51] Int. Cl.².................... C07F 1/10; C07C 51/00
[58] Field of Search............... 260/414, 430; 96/94, 96/96, 114.1, 114.6; 117/34, 36.9

[56] References Cited
UNITED STATES PATENTS

| | | | |
|---|---|---|---|
| 3,330,663 | 7/1967 | Weyde et al........................ | 96/114.6 |
| 3,458,544 | 7/1969 | Bryan................................. | 260/414 |
| 3,532,502 | 10/1970 | Boyer et al........................ | 96/114.6 |
| 3,713,833 | 1/1973 | Lindholm et al.................. | 96/114.1 |
| 3,767,414 | 10/1973 | Huffman et al.................... | 96/114.6 |
| 3,773,512 | 11/1973 | Poot et al. ......................... | 117/36.9 |
| 3,802,888 | 4/1974 | Willits................................ | 96/114.1 |
| 3,819,382 | 6/1974 | Konig et al. ....................... | 117/36.9 |
| 3,839,049 | 10/1974 | Simons................................ | 260/413 |

*Primary Examiner*—Winston A. Douglas
*Assistant Examiner*—P. E. Konopka
*Attorney, Agent, or Firm*—Sughrue, Rothwell, Mion, Zinn & Macpeak

[57] ABSTRACT

In a process for preparing organosilver carboxylates where an organic carboxylate aqueous solution is admixed with a water-soluble silver salt aqueous solution, a solvent which is difficultly soluble in water is present in the organic carboxylate aqueous solution. According to the process, organosilver carboxylates are obtained in the form of fine particles, which are useful for preparation of heat developable photographic materials.

20 Claims, No Drawings

3,960,908

PROCESS FOR PREPARING ORGANOSILVER CARBOXYLATES

BACKGROUND OF THE INVENTION

1. Field of the Invention

This invention relates to a process for preparation of organosilver carboxylates, in particular, to a process for preparation of fine particles of organosilver carboxylates which can advantageously be used in the manufacture of heat developable photographic materials.

2. Description of the Prior Art

Use of organosilver carboxylates as heat developable photographic materials has already been described, for example, in U.S. Pat. Nos. 3,589,901, 3,152,904, 3,457,075, and 3,589,903. These heat developable photographic materials essentially consist of an organosilver carboxylate such as silver behenate, a silver halide formed by the reaction of the silver salt with a halide or a silver halide separately formed and added, and a reducing agent.

After these heat developable photographic materials are exposed imagewise and then heated, silver images are formed due to the reaction of organosilver carboxylate and reducing agent caused by the catalytic action of the sensitized silver halide and the subsequent heating to follow.

A method for preparation of organosilver carboxylates which are suitable for manufacture of heat developable photographic materials is described for example in U.S. Pat. No. 3,458,544, where a solution of an organic carboxylic acid dissolved in a solvent which is difficultly soluble in water is admixed with an alkali-soluble silver complex aqueous solution to form fine organo silver carboxylate particles.

Organosilver carboxylates prepared by this method must necessarily be washed with water for the purpose of removing the alkali content contained in the silver complex aqueous solution. This is because, when organosilver carboxylates which have not been washed with water are used for manufacture of heat developable photographic materials, good images cannot be produced due to occurrence of strong fog in heat development.

However, even though the washing with water is carried out, the alkali content cannot completely be removed, and so it is impossible to completely prevent the occurrence of fog in heat development. Therefore, the use of an anti-fogging agent such as mercury compound has been inevitable, in order to obtain good image free from any fog. However, mercury compounds are toxic and so the use thereof is not desired.

In addition, the silver salts prepared by the method as described in U.S. Pat. No. 3,458,544 are further defective in that, when applied to a film, the materials are cloudy white. This is a fatal defect in manufacture of films for producing images which are to be observed using transmitted light.

SUMMARY OF THE INVENTION

Accordingly, an object of this invention is to provide a process for the preparation of organosilver carboxylates capable of producing heat developable photographic materials free from the occurrence of any fog even without the use of an anti-fogging agent such as a mercury compound, etc.

Another object of this invention is to provide a process for the preparation of organosilver carboxylates capable of being used on films and having extremely high transparency.

Still another object of this invention is to provide a process for the preparation of organosilver carboxylates for heat developable photographic materials in which the water washing step is unnecessary.

The present inventors have found after repeated research, that the objects of this invention can be attained by preparing organosilver carboxylates using a process where an organic carboxylate is reacted with a water-soluble silver salt in the coexistence of an aqueous solution of the organic carboxylate and a solvent which is difficultly soluble in water.

DETAILED DESCRIPTION OF THE INVENTION

The organic carboxylates suitable for the present invention are those whose silver salts are relatively stable to light. For example, long-chain aliphatic carboxylates having 10 or more carbon atoms up to about 24 carbon atoms, such as caprate, laurate, myristate, palmitate, stearate, behenate, etc., are suitable.

Organic carboxylates suitable for the present invention are preferably the alkali metal salts, the alkaline earth metal salts or the ammonium salts. Preferred salts are the alkali metal salts, such as the sodium salt and the potassium salt, and the ammonium salts.

Representative examples of these salts are, for example, sodium caprate, potassium caprate, ammonium caprate, magnesium caprate, sodium laurate, potassium laurate, ammonium laurate, sodium myristate, potassium myristate, ammonium myristate, sodium palmitate, potassium palmitate, ammonium palmitate, sodium stearate, potassium stearate, ammonium stearate, sodium behenate, potassium behenate, ammonium behenate, etc.

Suitable solvents which are difficultly soluble in water (i.e., having a solubility at 20°C of 10 parts or less,) preferably 2 parts or less by weight in 100 parts by weight of water, the esters of alcohols having from 1 to about 12 carbon atoms or phenols having from about 6 to 12 carbon atoms with phosphoric acid, phthalic acid or carboxylic acids which are liquid at normal temperature (about 20°–30°C) as well as, and in addition, aliphatic hydrocarbons having 5 to 12 carbon atoms and aromatic hydrocarbons are also useful. Suitable examples of such alcohols are butyl alcohol, ethanol, methanol, octyl alcohol, isoamyl alcohol, etc., and of such phenols are cresol, phenol, etc.

Typical examples of these solvents are as follows: tricresyl phosphate, tributyl phosphate, monooctyldibutyl phosphate, dimethyl phthalate, dioctyl phthalate, dimethoxyethyl phthalate, amyl acetate, isoamyl acetate, isobutyl acetate, isopropyl acetate, ethyl acetate, 2-ethylbutyl acetate, butyl acetate, propyl acetate, dioctyl sebacate, dibutyl sebacate, diethyl sebacate, diethyl succinate, propyl formate, butyl formate, amyl formate, ethyl valerate, diethyl tartrate, methyl butyrate, ethyl butyrate, butyl butyrate, isoamyl butyrate, pentane, hexane, heptane, cyclohexane, benzene, toluene, xylene, etc.

Water-soluble silver salts having a solubility of 0.2 g/100 g ($H_2O$) or more at 20°C, such as silver nitrate, silver perchlorate, silver sulfate or silver acetate are preferable as the water-soluble silver salts which can be used in the present invention.

In the present invention, it is preferable to react the silver salt and an emulsion of organic carboxylate aqueous solution and organic solvent which is difficultly soluble in water.

Various kinds of emulsification methods can be used in this invention, these methods are generally well known. Representative examples of these emulsification methods are the so-called "condensation method" where starting nuclei of extremely small diameters are grown into droplets of a desired size, and the so-called "dispersion method" where droplets of a large size are broken up into droplets of small size. Examples of these methods are those methods in which shakers, mixers, colloid-mills, homogenizers or ultrasonic waves are utilized.

The reaction temperature can freely be selected. However, if the reaction temperature is too high, the solvent used boils, which is disadvantageous. In general, the reaction temperature is preferably in the range of 70°C or below, e.g., from about −10° to 70°C, preferably 0° to 70°C.

The concentration of solution can also be selected freely. A suitable range can be from about 0.01 to 6 N, preferably 0.1 to 4 N for the silver salt and from about 0.05 to 50 percent, preferably 0.1 to 30 percent, by weight for the carboxylic acid salt. In addition, the speed for addition of the solution also is optional.

The method and condition for stirring of the reaction solution can also be selected freely.

In addition, the steps of the method of the present process can be optionally selected. That is, various steps and orders can be employed, including a method where a water-soluble silver salt solution is added to an organic carboxylate aqueous solution containing an organic solvent which is difficultly soluble in water, and then reacted therewith; a method where an organic carboxylate aqueous solution containing an organic solvent which is difficultly soluble in water is added to a water-soluble silver salt solution, and then reacted therewith; and a method where a water soluble silver salt solution and an organic carboxylate aqueous solution containing an organic solvent which is difficultly soluble in water are added at the same time and reacted with each other, and like methods.

In the organic solvent (which is difficultly soluble in water) present in the organic carboxylate aqueous solution, a compound which can form a silver salt by the reaction with silver ion can also be present, e.g., in an amount of about $10^{-6}$ to $10^{-1}$, preferably $10^{-4}$ to $10^{-2}$ mol per mole of silver ion, such as a heterocyclic mercapto compound, e.g., 1-phenyl-5-mercaptotetrazole, an imino group containing heterocyclic compound, e.g., benzotriazole or phthaladinone, or an organic carboxylic acid, e.g., behenic acid, stearic acid, palmitic acid, myristic acid, lauric acid or capric acid.

Manufacture of organic silver salts of the present invention preferably comprises the following steps.

1. The organic carboxylate is dissolved in water.
2. The organic solvent which is difficultly soluble in water is added to the solution obtained in the step (1) above to form an emulsion.
3. The water-soluble silver salt is dissolved in water.
4. The solutions of the steps (2) and (3) above are admixed and reacted with each other.
5. The organosilver carboxylate formed is separated. (In this separation, any conventional method can be employed, for example, decantation, filtration, centrifuging, etc.).

Using the thus prepared organosilver carboxylate fine crystals, heat developable photographic materials can be produced which are composed of a heat developable photographic composition coated on a support, for example, in a dry thickness ranging from about 0.05 $\mu$ to 6 $\mu$, with the composition comprising the following components:

1. an organosilver carboxylate prepared in this invention,
2. a catalytic amount of a photosensitive silver halide, for example, a silver halide prepared by the reaction of an organosilver carboxylate and an inorganic or organic halide,
3. a reducing agent (a compound) which reduces the organosilver carboxylate to produce a silver image, when heated in the presence of the sensitized silver halide), and
4. binder.

Examples of heat developable photographic materials are disclosed in U.S. Pat. Nos. 3,457,075, 3,589,903 and 3,761,279.

The heat developable photosensitive layer can further contain the following additives: blackening agents to darken further the obtained image, for example, mercapto compounds, azole-thions and phthalazinones; development accelerators, for example, carboxylic acids or compounds which display a basic character after being heated, such as oxalic acid-amine salt; inorganic oxides or hydroxides; reducing agents such as photolytic reducing agent, for example, a compound which accelerates the photolysis of an ascorbic acid ester when this ester is used, such as benzil, as well as a spectral sensitizing dye capable of imparting sensitivity to light of a long wavelength, for example, merocyanine dyes, rhodacyanine dyes, acid dyes and cyanine dyes which contain thiohydantoin nuclei or rhodanine nuclei.

In heat developable photographic materials, for example, as described in Japanese patent publication Nos. 22185/70, 41865/71 and 4924/68 and U.S. Pat. Nos. 3,589,901 and 3,589,903, when organosilver carboxylate fine particles prepared according to the process of this invention are used as the organic silver salt, the following two aspects are remarkably improved:

1. Development fog hardly occurs during heat development

When organosilver carboxylates prepared according to conventional methods (for example, as described in U.S. Pat. No. 3,458,544) are used, development fog tends to occur very often in heat development, and therefore, anti-fogging agents such as a mercury compound is necessarily used. Whereas, the heat developable photographic materials prepared by using the organosilver carboxylate of the present invention suprisingly do not require any anti-fogging agent such as a mercury compound. This is extremely important improvement in heat developable photographic materials in that mercury compounds which are toxic are not used.

2. The coating material on film is very transparent

When an organosilver carboxylate prepared according to conventional methods (for example, as described in U.S. Pat. No. 3,458,544) is applied to a film, the coated film becomes cloudy and opaque. Whereas, when the organosilver carboxylate prepared according to the present process is applied to a film, the coated film is surprisingly transparent. On these grounds, the organosilver carboxylates of the present invention are extremely advantageous in the production of films for transparencies.

In addition, great improvements are attained in the manufacturing. That is, in the conventional process for preparing organosilver carboxylates, it has been necessary to wash the products with water extremely carefully so as to remove water soluble salts and excess alkali content. Such water-washing step is unnecessary in the process for preparing organosilver carboxylates of the present invention. This is extremely significant when a large amount of organosilver carboxylates are to be prepared.

That is to say, it is extremely meaningful from the standpoint of preventing environmental pollution in that no washed wastes occur. In addition, the manufacturing is extremely simplified due to the absence of the water-washing step, whereby the costs of the products can possibly be lowered.

Now, the present invention will be explained in greater detail in the following Examples. Unless otherwise indicated, all parts, percents, ratios and the like are by weight.

EXAMPLE 1

3.6 g of sodium behenate were dissolved in 2000 ml of water at 60°C and this solution was adjusted to 45°C. 100 ml of tricresyl phosphate adjusted to 45°C were added thereto, and the resulting solution was subjected to ultrasonic waves of 20 KHz 45 W for 10 minutes in an ultrasonic apparatus (UR-150P manufactured by Tominaga Manufacturing Co.) to prepare an emulsion. To this was added an aqueous solution (45°C) of 1.7 g silver nitrate dissolved in 100 ml of water while stirring.

The silver salt and tricresyl phosphate solidified in the form of an oleaginous mixture was separated and collected.

Next, the following heat developable photographic composition was prepared with the silver behenate, which was then applied to a polyethylene terephthalate film support in an amount of 1.2 g of silver per square meter to produce a heat developable photographic material.

| | |
|---|---|
| Silver Salt-Polymer Dispersion* | 40 ml |
| Solution of 0.9 g of Zinc Bromide Dissolved in 20 ml of Methanol | 1.2 ml |
| Acetone Solution Containing 0.02 wt% Benzoxazolilidene-thiohydantoin (sensitizing dye) | 1 ml |
| 25 wt% Ethyleneglycol Monomethylether Solution of 2,2'-Methylenebis(6-t-butyl-4-methylphenol) | 8 ml |
| Ethyleneglycol Monomethylether Solution Containing 10 wt% Phthaladinone | 8 ml |

*Preparation of the silver salt-polymer dispersion: 5 g of silver salt were added to 40 ml of isopropyl alcohol solution containing 4 g of polyvinyl butyral, and subjected to ball-milling for 4 hours to form a dispersion.

The thus manufactured photographic material was transparent. This material was exposed in an exposure amount of $10^5$ SMS to a tungsten lamp through a transparent negative original having gradations, and heated at 120°C for 10 seconds to obtain a positive image having gradations (maximum density (Dmax) = 1.7; fog = 0.05).

When this photographic material was heated at 120°C, the time until the occurrence of fog of a density of 0.08 was 20 seconds.

COMPARATIVE EXAMPLE 1

3.4 g of behenic acid were dissolved in 100 ml of tricresyl phosphate at 60°C and this was adjusted to 45°C. To this were added 100 ml of distilled water adjusted to 45°C, and then the solution was subjected to ultrasonic waves of 20 KHz 45W for 10 minutes in an ultrasonic apparatus (UR-150P manufactured by Tominage Manufacturing Co.).

To the resulting system were added 100 ml of an aqueous solution (45°C) of silver-ammonium complex while stirring. (The aqueous solution of the silver-ammonium complex was prepared as follows: Aqueous ammonia was added to about 80 ml of an aqueous solution containing 1.7 g of silver nitrate and then water was added thereto to make total volume 100 ml of the silver-ammonium complex/aqueous solution.)

The silver salt was separated and collected by filtration, and then washed with 400 ml of distilled water. This washing operation was repeated four times, and then the salt was again washed with 400 ml of methanol.

Finally, the silver behenate formed was separated and collected by centrifuging.

Using the resulting silver salt, a heat developable photographic material having the same composition as described in Example 1 was produced using the same procedures of Example 1.

The thus manufactured photographic material was cloudy white and opaque.

After the material was treated under the same conditions as in Example 1, a positive image (Dmax = 1.9; fog = 0.5) was obtained.

The heating time until the occurrence of fog of a density of 0.08 was 3 seconds.

Apart from this, another material was prepared in which 0.5 ml of a methanol-mercuric bromide solution (containing 0.1 g of mercuric bromide dissolved in 20 ml of methanol) was further added in addition to the above composition. When this material was heated at 120°C, the time until the occurrence of fog of a density of 0.08 was 15 seconds.

EXAMPLE 2

11 g of potassium laurate were dissolved in 200 ml of water at 60°C and this solution was adjusted to 20°C. 100 ml of isoamyl acetate adjusted to 20°C were added thereto and vigorously shaken to form an emulsion.

To this was added an aqueous solution (20°C) of 8.5 g of silver nitrate dissolved in 100 ml of distilled water while stirring.

The silver laurate and isoamylacetate solidified in the form of an oleaginous mixture was separated and collected. To this were added 500 ml of methanol and the mixture was vigorously shaken. Then silver laurate was separated and collected by centrifuging.

A heat developable photographic composition having the following components was prepared using the resulting silver laurate, and this composition was applied to a polyethylene terephthalate film support in an amount of 1.3 g of silver per square meter to produce a heat developable photographic material.

| | |
|---|---|
| Silver Salt-Polymer Dispersion* | 45 ml |
| Ammonium Bromide (5 wt% methanol solution) | 0.8 ml |
| Methanol Solution of 0.025 wt% Tetrachloro-tetrabromofluorescein Acid Dye | 0.6 ml |
| Phthaladinone (5 wt% ethyleneglycol monomethyl-ether solution) | 1.2 ml |
| p-Phenylphenol (70 wt% ethyleneglycol | 8 ml |

-continued

| monomethylether solution) |
| --- |

*Preparation of the silver salt-polymer dispersion: 5 g of silver salt were added to 40 ml of an isopropyl alcohol solution containing 4 g of polyvinyl butyral and then subjected to ball-milling for 4 hours to form a dispersion.

The thus produced photographic material was transparent. This material was exposed in an exposure amount of $10^5$ CMS to a tungsten lamp through a transparent negative original having gradations, and heated at 120°C for 8 seconds to obtain a positive image having gradations (Dmax = 1.8; fog = 0.04).

When this photographic material was heated at 120°C, the time until the occurrence of fog of a density of 0.08 was 15 seconds.

COMPARATIVE EXAMPLE 2

11 g of lauric acid were dissolved in 100 ml of isoamyl acetate at 60°C and this mixture was adjusted to 20°C. To this mixture were added 100 ml of distilled water adjusted to 20°C, and the solution was subjected to ultrasonic waves of 20 KHz 45 W for 10 minutes in an ultrasonic apparatus (UR-150P manufactured by Tominage Manufacturing Co.).

To this were added 100 ml of an aqueous solution of silver-ammonium complex (20°C) while stirring. (The complex solution was prepared as follows: 8.5 g of silver nitrate were dissolved in about 80 ml of distilled water and aqueous ammonia was added thereto to form the silver-ammonium complex, and then distilled water was added to make the total volume 100 ml of aqueous solution.)

The silver salt was separated and collected by filtration and then washed with 400 ml of distilled water. This operation was repeated four times, and then the salt was again washed with 400 ml of methanol.

Finally, the silver laurate formed was separated and collected by centrifuging.

Using the thus prepared silver laurate, a heat developable photographic composition having the same components as described in Example 2 was prepared, which was then applied to a polyethylene terephthalate film support to produce a heat developable photographic material using the procedure of Example 2.

This photographic material was opaque.

After this material was treated under the same conditions as described in Example 2, a positive image (Dmax = 1.9; fog = 0.9) was obtained.

The time until the occurrence of fog of a density of 0.08, when the material was heated at 120°C, was 2 seconds.

A part from this, another material was prepared in which 0.2 ml of a methanol-mercuric bromide solution (containing 0.1 g of mercuric bromide dissolved in 20 ml of methanol) was further added in addition to the above composition. When this material was heated at 120°C, the time until the occurrence of fog of a density of 0.08 was 13 seconds.

EXAMPLE 3

11 g of sodium laurate were dissolved in 200 ml of water at 60°C and this was adjusted to 20°C.

On the other hand, 1.5 g of lauric acid were dissolved in 100 ml of isoamyl acetate and this was adjusted to 20°C. These two solutions were admixed and vigorously shaken to form an emulsion. To this emulsion was added an aqueous solution of 8.5 g of silver nitrate dissolved in 100 ml of distilled water (20°C) while stirring.

The silver laurate and the isoamyl acetate solidified in the form an oleaginous mixture was separated and collected.

Using the resulting silver laurate, a heat developable photographic composition having the same components as described in Example 2 was prepared, which was then applied to a baryta paper in an amount of 1.3 g of silver per square meter to produce a heat developable photographic material.

The thus manufactured material was exposed in an exposure amount of $10^5$ CMS to a tungsten lamp through a transparent negative original having gradations and then heated at 120°C for 5 seconds, whereby a positive image (Dmax = 2.4; fog = 0.06) was obtained.

While the invention has been described in detail and with reference to specific embodiments thereof, it will be apparent to one skilled in the art that various changes and modifications can be made therein without departing from the spirit and scope thereof.

What is claimed is:

1. A process for preparing organosilver carboxylates comprising mixing:
    a. an emulsion of a solvent having a solubility at 20°C of less than two parts by weight in 100 parts of water, which solvent is selected from the group consisting of the esters of alcohols or phenols with phosphoric acid, phthalic acid or a carboxylic acid, which are liquid at normal temperatures, aliphatic hydrocarbons and aromatic hydrocarbons, with an aqueous solution of an organic carboxylate selected from the group consisting of alkali metal, alkaline earth metal, and ammonium salts of long chain aliphatic carboxylic acids having 10 or more carbon atoms whose silver salt is relatively stable to light, and
    b. an aqueous solution of a silver salt having a solubility at 20°C of at least 0.2 g per 100 g of water;
said mixing taking place at a temperature below the boiling point of said solvent.

2. The process as claimed in claim 1, wherein said organic carboxylate is selected from the group consisting of an alkali metal salt, or an ammonium salt of said long-chain aliphatic carboxylic acid.

3. The process as claimed in claim 2, wherein said long-chain aliphatic carboxylic acid salt is the caprate, laurate, myristate, palamitate, stearate or behenate salt.

4. The process as claimed in claim 1, wherein said organic carboxylate is an alkaline earth metal salt of said long-chain aliphatic carboxylic acid.

5. The process as claimed in claim 4, wherein said long-chain aliphatic carboxylic acid salt is the caprate, laurate, myristate, palamitate, stearate or behenate salt.

6. The process as claimed in claim 2, wherein said salt is selected from the group consisting of sodium caprate, potassium caprate, ammonium caprate, sodium laurate, potassium laurate, ammonium laurate, sodium myristate, potassium myristate, ammonium myristate, sodium palmitate, potassium palmitate, ammonium palmitate, sodium stearate, potassium stearate, ammonium stearate, sodium behenate, potassium behenate and ammonium behenate.

7. The process as claimed in claim 1, wherein said solvent is selected from the group consisting of isopropyl acetate, ethyl acetate, propyl acetate, propyl formate or methyl butyrate.

8. The process as claimed in claim 1, wherein said solvent is selected from the group consisting of tricresyl phosphate, tributyl phosphate, monooctyldibutyl phosphate, dimethyl phthalate, dioctyl phthalate, dimethoxyethyl phthalate, amyl acetate, isoamyl acetate, isobutyl acetate, 2-ethylbutyl acetate, butyl acetate, dioctyl sebacate, dibutyl sebacate, diethyl sebacate, diethyl succinate, butyl formate, amyl formate, ethyl valerate, diethyl tartrate, ethyl butyrate, butyl butyrate, isoamyl butyrate, pentane, hexane, cyclohexane, heptane, benzene, toluene, and xylene.

9. The process as claimed in claim 1, wherein said water-soluble silver salt is silver nitrate, silver perchlorate, silver sulfate or silver acetate.

10. The process as claimed in claim 1, wherein said solvent contains a compound capable of forming a silver salt by the reaction with silver ion, said compound containing a mercapto group, an imino group, or an organic carboxylic group.

11. The process as claimed in claim 10, wherein said compound capable of forming a silver salt is 1-phenyl-5-mercaptotetrazole, benzotriazole, phthaladinone, behenic acid, stearic acid, palmitic acid, myristic acid, lauric acid or capric acid.

12. The process as claimed in claim 1, including the following steps: (1) dissolving said organic carboxylate in water, (2) adding said solvent to the solution obtained in the step (1) above to form an emulsion, (3) dissolving a water-soluble silver salt in water, (4) mixing the solutions of the above steps (2) and (3) so as to and react with each other, and (5) separating the organosilver carboxylate formed.

13. The process as claimed in claim 2, wherein said organic carboxylate is an alkali metal salt of said long-chain carboxylic acid.

14. The process as claimed in claim 1, wherein said mixing takes place at a temperature in the range of $-10°$ to $70°C$.

15. The process as claimed in claim 1, wherein the concentration of silver salt in (b) is from 0.01 to 6N.

16. The process as claimed in claim 15, wherein the concentration of silver salt in (b) is from 0.1 to 4N.

17. The process as claimed in claim 1, wherein the concentration of organic carboxylate in the aqueous solution of (a) is from 0.05 to 50 percent by weight.

18. The process as claimed in claim 17, wherein the concentration of organic carboxylate in the aqueous solution of (a) is from 0.1 to 30 percent by weight.

19. The process as claimed in claim 10 wherein said compound capable of forming a silver salt is present in an amount of about $10^{-6}$ to $10^{-1}$ mol per mol of silver ion.

20. The process as claimed in claim 19 wherein said compound capable of forming a silver salt is present in an amount of from about $10^{-4}$ to $10^{-2}$ mol per mol of silver ion.

* * * * *